US007699752B1

(12) United States Patent
Anderson et al.

(10) Patent No.: US 7,699,752 B1
(45) Date of Patent: *Apr. 20, 2010

(54) EXERCISE ACTIVITY RECORDING SYSTEM

(76) Inventors: Brent Anderson, 2047 Rose Point La., Kirkland, WA (US) 98033; Douglas Nichols, 24611 NE. Patterson Way, Redmond, WA (US) 98053

( * ) Notice: Subject to any disclaimer, the term of this patent is extended or adjusted under 35 U.S.C. 154(b) by 0 days.

This patent is subject to a terminal disclaimer.

(21) Appl. No.: 12/383,469

(22) Filed: Mar. 23, 2009

Related U.S. Application Data

(63) Continuation-in-part of application No. 10/819,052, filed on Apr. 6, 2004, now Pat. No. 7,507,183.

(60) Provisional application No. 60/461,204, filed on Apr. 7, 2003.

(51) Int. Cl.
*A63B 15/02* (2006.01)
(52) U.S. Cl. .................. 482/1; 482/8; 482/9; 705/2
(58) Field of Classification Search ............. 482/1–9, 482/900–902; 434/247; 601/23; 705/1–3
See application file for complete search history.

(56) References Cited

U.S. PATENT DOCUMENTS

| 5,947,869 | A * | 9/1999 | Shea | 482/8 |
|---|---|---|---|---|
| 6,702,719 | B1 * | 3/2004 | Brown et al. | 482/8 |
| 6,793,607 | B2 * | 9/2004 | Neil | 482/8 |
| 6,796,927 | B2 * | 9/2004 | Toyama | 482/8 |
| 6,827,670 | B1 * | 12/2004 | Stark et al. | 482/9 |
| 7,056,265 | B1 * | 6/2006 | Shea | 482/8 |
| 2001/0053735 | A1 * | 12/2001 | Cohen et al. | 482/902 |
| 2002/0086774 | A1 * | 7/2002 | Warner | 482/8 |
| 2003/0158014 | A1 * | 8/2003 | Valentin-Sivico | 482/8 |
| 2003/0226695 | A1 * | 12/2003 | Mault | 177/25.16 |
| 2005/0064995 | A1 * | 3/2005 | Shitan | 482/8 |

* cited by examiner

*Primary Examiner*—Glenn Richman
(74) *Attorney, Agent, or Firm*—Dean A Craine

(57) ABSTRACT

A multiple exercise activity recording system in which each piece of equipment, exercise movement exercise area, fitness activity or biometric in a facility where exercises are preformed is assigned to an exercise identification module. Each exercise identification module is linked or coupled to a terminal with a display and a manual input device. Each user is assigned a personal identification device that is presented or inputted into the terminal before or after the exercise equipment or exercise area is used. After exercising, the user activates the exercise identification module assigned to the exercise equipment or to the exercise area. Upon activation, one or more sub-routines automatically run in the terminal. Prompts presented on the display then request user input of information pertinent to the exercise activity. The inputted information may be stored in the terminal or immediately transmitted to a permanent member data file on a local or remote server.

13 Claims, 6 Drawing Sheets

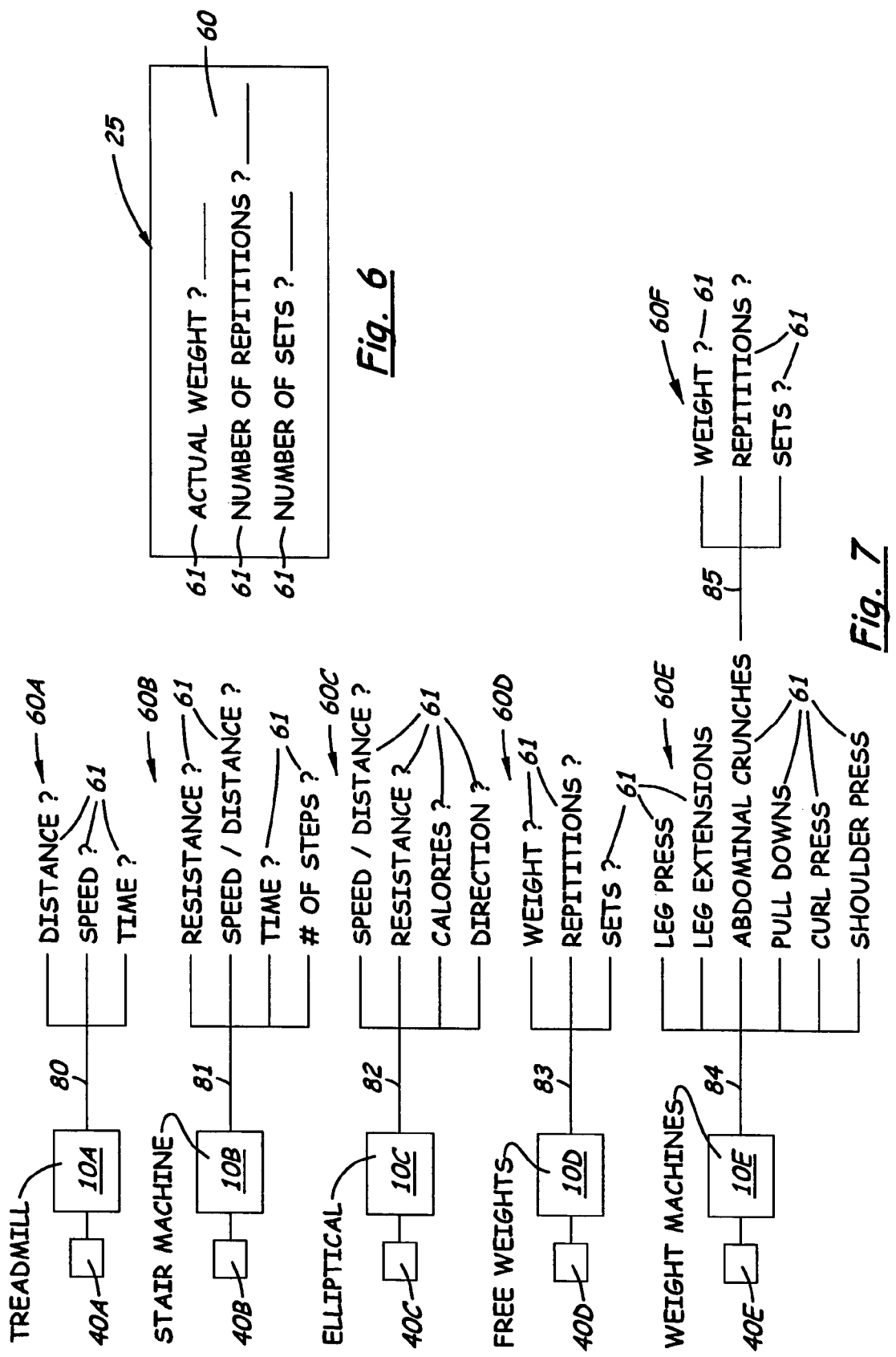

EXERCISE ACTIVITY RECORDING SYSTEM

This utility patent application is a continuation in-part application of the Utility U.S. Pat. No. 7,507,183, issue date Mar. 24, 2009, (Ser. No. 10/819,052), filed Apr. 6, 2004 which is based on the provisional patent application (Ser. No. 60/461,204) filed on Apr. 7, 2003.

BACKGROUND OF THE INVENTION

1. Field of the Invention

This invention relates to exercise metrics recording systems, and more particularly, to exercise metrics recording systems located in health club/gym facilities that offer different pieces of exercise equipment and exercise activities to its members.

2. Description of the Related Art

There are approximately 22 thousand fitness centers and health clubs in the United States serving approximately 40 million members. The health club industry is characterized by rapid growth in club members (8% per annum) and an explosion in exercise related activities and equipment. There has also been tremendous growth in information related to the optimal use of exercise equipment including: the best use of time devoted to exercise, long term impact of specific exercise activity, avoidance of injury, and preferred combinations of exercises.

To help individual health club members maximize the benefit of time spent exercising, most health clubs offer professional training services. Professional training services support the goals of maximizing the benefit of time expended toward exercise, injury avoidance, and maintaining a long-term focus to a given exercise regime. Professional training services (as currently offered) require the trainer to directly participate in his or her clients' exercise sessions to observe and track activity and performance. Direct participation by the professional trainer in most or all of his or her clients' exercise sessions carries with it a number of negative attributes, including very high service costs, advance scheduling requirements for exercise sessions, regimentation of recreational workout activity into 'hard core' training sessions and, for some, a 'loss of privacy' in exercise activity that many health club members view negatively.

An effective exercise metrics recording system enabling individuals to independently record their exercise activity in a digital format would permit fitness professionals to effectively counsel and/or train the individual system member without necessitating the trainer's direct participation in each of the client's day to day workouts. Such an exercise metrics recording system would also eliminate advance scheduling and aesthetic problems associated with the use of professional training services. Most important, such an exercise metrics recording system would permit professional counseling services to be rendered more efficiently at prevailing price levels, and enable health clubs to provide a much broader range of fitness training/counseling services to address the needs and price constraints of the majority of health club members. Finally, the digital exercise and fitness records produced by such an exercise metrics recording system could be provided to third parties not affiliated with the health club or fitness center, such as doctors, therapists, managed healthcare providers, corporate wellness program administrators, etc., who have an interest in the health and well-being of particular health club members.

Two basic approaches have been attempted toward the goal of recording exercise activity onto a digital medium: "active network systems" and "scripted training systems."

Active network systems deploy a local electronic network in the health club with each exercise machine equipped with a display monitor, data input means and sensors, and operating as a data collection node. The health club member identifies himself or herself to a particular machine or workout station via entry of a personal identification number on a key pad at the workout station. Upon completion of the exercise, certain performance information collected by sensors at the workout station is transmitted to a central server where individual exercise records are stored. Active network systems are effective where exercise equipment operates at a fixed location in the gym or fitness center, and where each piece of exercise equipment in the network supports only one or two exercise movements.

Active network systems encounter problems dealing with any equipment that is mobile or capable of being employed in multiplicities of exercise movements. Free weights are the most obvious example of exercise equipment that cannot be linked in an active network system. In addition to problems accommodating data input from some types of exercise equipment, active network systems do not support tracking of activity-related exercise (e.g., aerobic dancing; running; basketball; etc). Additionally, the provisioning of electrical power to active networked systems and the installation of network monitors, data input means, and sensors at each piece of the networked equipment result in high capital installation costs and high recurring maintenance costs. Active network systems are also costly to expand as new exercise machines and methods are brought into the health club.

The second means to record exercise-related activity involves the use of dedicated software programs operating on PDAs or similar handheld devices. Exercise software programs fall into two categories: "menu-driven database programs" and "scripted exercise routine systems."

Exercise menu-driven programs involve simple database lookup programs applied to the tracking of fitness activity. Using a PDA or similar handheld device, the health club member scrolls through a preprogrammed menu of commonly available exercises, identifies his or her intended exercise activity, and enters certain performance information into the handheld device upon completion of the exercise. The principal problem with menu-driven database programs as applied to health and fitness records is the length and complexity of the menu necessary to accommodate the literally thousands of exercise options available in a typical health club. The burden of cycling through available workout options to locate the desired entry point in the database program has rendered menu-driven database programs too burdensome for most health club members and impractical as effective exercise metrics tracking systems. U.S. Pat. Nos. 4,493,485; 4,409,992; 4,408,183; and 5,890,997.

Scripted exercise records systems exist in multiple forms. In their simplest embodiment, a piece of paper can be carried through a work out with an exercise program written on it, as the User follows the prescribed routine he/she checks boxes and writes down performance data. Systems have been developed to simplify the task of data entry and data conversion into a digital format by introducing a PDA or similar handheld device configured to store user exercise performance data relative to an exercise script which is carried on the PDA like device or recorded on a work out card to be read by the PDA. There are many number of innovations relative to script based exercise records systems, but the identification of these script based exercise record systems as "related art" is problematic. Scripted systems simply do not meet the challenge of identifying what exercise activity/s a User elected to perform during a given work out. Rather than address the multiple thousands of combinations related exercise data source, and possible combinations of weight used, repetitions completed, time, distance, speed, resistance level etc., scripted systems allow the User to record performance against a narrowly defined exercise program. The user performs the prescribed exercise and then records certain performance information by hand or into a PDA or similar handheld device which contains the exercise script. The limitations placed on data input sources by script based exercise records systems represent a fundamental difference relative to the subject invention and other "related art" described herein. Script-based exercise systems necessarily require members to strictly follow a prescribed training program in order to track performance. While most health club members follow generalized patterns in their exercise and recreation The majority of health club members do not strictly follow training programs, (The average health club member being over 30 years old and more interested in maintaining a reasonable level of fitness than running a marathon or "body sculpting". Accordingly, script-based systems have enjoyed limited acceptance among health club members. Finally, while Script based systems are not precisely "related art," a second issue is worth noting that has kept these systems from enjoying wide applications in the health and fitness club market.

An exercise script for a PDA can be written by anyone for use by a health club member in the gym. While the health club operator can control perimeter facility access, the health club operator cannot control access to individual exercise apparatus or compel the use of his or her club based training services in conjunction with the script based system. In fact, script based exercise records systems operate to introduce internet/non resident trainer competition into a health club, threatening a major revenue source for the typical health club. The end result being relegation of script based systems to treatment related exercise programs (Health care provider prescribed) and limited acceptance by interne trainers.

A need exists for a new exercise metrics collection system for a health club capable of collecting, transferring, storing, and managing individual exercise records of its members, without the operating restrictions and high costs described herein above. The new system will differ from existing methods, offering its members easy and flexible operation unencumbered by scripted exercise routines which are directive in nature. Such a system should accept data input from any fitness data source including activity-based workouts (e.g., aerobic dancing; running; basketball; etc.), stretching, all forms of resistance training (including exercises using freeweights), and biometric monitoring devices. In addition system should be materially less expensive to install and maintain than are active network systems, and must provide for control over access to the system, particularly its exercise identification component

SUMMARY OF THE INVENTION

It is an object of the present invention to provide an inexpensive, easy to use exercise recording system specifically designed for use in a health club and other sports and fitness facilities which offers different pieces of exercise equipment and exercise activities to its members.

It is another object of the present invention to provide such a system that uses handheld devices or terminals that allow members to easily record various exercise activities in the facility.

It is another object of the present invention to provide such a system that provides exercise machine or exercise activity related sub-routines to the member that instructs the member regarding the type of data to be inputted into the handheld device to terminal by the member after the exercise is completed.

It is another object of the present invention to provide such a system that allows health club trainers the option to selectively program the handheld device or terminal for specific members instructing the members to include or more specific types of exercise and the exercise level to be preformed on those recommended exercises.

It is another object of the present invention to provide such a system that is relatively inexpensive to assemble, install and maintain.

It is another object of the present invention to provide such a system that uses only handheld devices or terminals that are uniquely configured and provided by the health club for use in the health club.

It is another object of the present invention to provide such a system that does not require the direct participation of a trainer during or after every exercise session.

It is another object of the present invention to provide such a system that does not require a member to perform exercise activity according to a prescribed sequence.

It is another object of the present invention to provide such a system that can be linked to other health clubs so that members' exercise records may be aggregated and quantitatively or qualitatively evaluated, and shared.

It is another object of the present invention to provide such a system that can centrally store, protect and discretely distribute individual exercise records in such a way as to allow individual records to address member exercise activity preformed away from the member's home gym and further to allow for the distribution of individual exercise records to interested and authorized third parties (healthcare providers, weight loss clinics, insurance providers, DoD [force readiness] Etc.)

It is another object of the present invention to provide such a system that can deploy statistical analysis and data base tools against a centrally stored collection of, individual exercise records to provide business and public interest related data mining against the system's population of individual records.

It is another object of the present invention to provide such a system that deploys software tools which apply statistical analysis and fitness related information/principles against an individual's exercise records to aid in maintaining safe and effective exercise patterns.

These objects are met by an exercise activity records system disclosed herein that enables users to easily record different exercise activities performed in the facility. In a first embodiment, the system includes a portable handheld device capable of being pre-programmed by the trainer for a specific member that is then used by the member to record exercise activities. The system also includes a unique identifying "exercise identification module", hereinafter referred to as an EIDM, attached to or located in the proximate vicinity of an exercise activity source. The handheld device includes a display monitor, a data input means, and an EIDM interrogation means used query the EIDM. During use, the member activates the handheld device which executes an exercise data collection software program loaded into the working memory of the handheld device. When the member selects a piece of exercise equipment or an exercise activity, (e.g. weight lifting), the EIDM interrogation means is activated and used to interrogate the EIDM. When the EIDM is identified, the exercise data collection software program automatically executes a software sub-routine specifically designed for the individual and the specific exercise activity source associated with the EIDM. More specifically, the sub-routine presents a data entry page on the display monitor. The data entry page identifies the exercise machine or activity, the type of exercise to be completed, and presents a plurality of prompts requesting specific information from the member regarding the exercise activity performed on the exercise activity data source. The information that is inputted into the handheld device using the input means is directly stored in a temporary member data file on the handheld device or transmitted directly to a permanent member file stored on a local server located in the health club. If the information is stored in a temporary member data file on the handheld, it is later uploaded to the local server. Each time the member moves to a new exercise data activity source, the EIDM interrogation means and the EIDM are used to quickly identify the exercise activity data source and present the proper sub-routine associated with the exercise activity.

In another embodiment of the invention, the exercise activity source in the facility where exercises are preformed is assigned to an EIDM but each EIDM is linked or coupled to a stationary terminal connected to or located near the exercise activity source. The terminal, which may be linked exclusively to one exclusively exercise activity source and one EIDM or may be linked to multiple exercise activity sources and EIDMs, is connected to a display and an optional manual input device. The EIDM associated with each exercise activity source may be located at or near the exercise activity source or it may be mounted on the terminal's front panel or on a multiple exercise activity demonstration board. Loaded into the memory of the terminal is an exercise data collection software program and user data file.

Each user is assigned a personal identification code which must be manually inputted into the terminal or assigned an electronic identification device that interfaces with the EIDM or another compatible input device to input the user's identification into the terminal. The personal identification code or electronic identification device transmits the user's identification information to the terminal before or after the exercise equipment or exercise area is used. An example of an electronic identification device assigned to a user is an I-button. During use, the user's I-button is pressed against a compatible, terminal linked I-button connected or linked to the terminal that automatically transmits the user's personal identification code into the terminal. In the preferred embodiment, the terminal I-button also acts as an EIDM, which, when activated by the user's I-button, automatically informs the terminal which exercise activity source is selected and also informs the terminal of the user's identification information.

After exercising, the user activates the EIDM associated with the exercise activity source. When the EIDM is activated, a sub-routines and prompts relating to the exercise are then presented on the terminal's display. The user then manually inputs exercise specific information into the terminal in response to the prompts.

The key differences between the first and second embodiments, is that mobile and fixed components of the system are reversed. In the first embodiment, after the EIDM is activated, a data exchange sequence is initiated by the handheld. In the second embodiment, when the user activates the EIDM, a data exchange sequence is initiated in the terminal. In both embodiments, a sub-routine specific to the exercise activity source is automatically generated. In the second embodiment, the identification sequence is directed towards identifying the user to the terminal and to the specific exercise selected by the system user. The EIDM is now in a fixed location as are the terminal with the exercise date program, the exercise specific sub-routines and the processor. The only mobile component is the user's identification codes or input device. Also, inputted information may be stored in the terminal or immediately transmitted to a permanent member data file on a local or remote server In both embodiments, the system may includes a local server located in the facility with permanent member data files that contains the inputted records from the handheld devices or terminals used by members in the club. In another embodiment, the local server is replaced by an uplink terminal connected to a remote server located in a network operations center, hereinafter referred to as a NOC, that via the Internet. In both embodiments, a data base software program designed to collect the uploaded records in the handheld device's or terminal's temporary member data file and then present the information to the trainer and/or member when connected to the server.

The system will also use a tool set of software programs, hereinafter referred to as a 'tool set', which support data colorations unique to exercise metrics and associated directly or indirectly to the member's specific workout history. The system will cross track and display to the health and, fitness professional any number of relationships and data correlations to the member's work outs. In addition, the tool set will maintain and display state of the art information to fitness professional counseling the member identifying areas of concern/progress and offering alternative course of action (in terms of exercise) to effectively counsel the member relative to his/her exercise regime.

Using the above-described device, a method of recording the exercise routines in a health club, an exercise facility or medical facility is also provided. During use, the member selects a health club or facility with different exercise activity data sources each associated with a unique EIDM. When the member visits the health club or facility, he or she may be provided a handheld device as describe above loaded with various software sub-routines associated with the EIDMs or a user identification code. As the member moves throughout the health club or facility, he or she performs various exercise activities, and inputs data in response to the sub-routine prompts. When the exercise activity is completed, the temporary member data file on the handheld device or terminal is uploaded to the local server or to the remote server on the NOC. The fitness data base software program on the local server or remote server is then used by the trainer to review a member's data file. The tool set provides the trainer access to the most recent information relative that members exercise needs as well as a backup to the trainer's own record review insuring that all areas of concern have been identified and addressed by the trainer relative to the member.

The subject invention deployed an architecture which is unique and novel relative to the collection of individual workout information in a health club environment.

Unlike the prior art active network systems identified herein, the subject invention deploys a handheld or a terminal to collect individual exercise records with this step the subject invention becomes an order of magnitude cheaper than active network systems. With the elimination of the active network approach the subject invention becomes far more flexible in its operation, allowing the system to breakaway from fixed machine limitations of active network systems to embrace free weights, basketball, running, handball etc. (and activity which can be expressed as a numeric.

Deployment of a handheld or a terminal in the system together with an EIDM with which the handheld or terminal shares a relationship and the location of that EIDM on or around its represented exercise activity source allows the user to gather data from anywhere in the health club or facility any time in any order. In this manner, the invention is not confined to a scripted workout and allows him/her to simply approach and query the EIDM for the exercise intended rather than run through multiple menus or fumble through a phone book of optical symbol tag/RFID tags to tell the data collection device what exercise the member intends to do next to further the subject invention.

By using unique identifiers relative to each exercise activity source at a specific site, and by providing an "encrypted" response/disclosure capability for each EIDM, access to the system becomes controllable. The subject invention becomes potentially profitable to the health club therefore available to members in a health club environment.

The over aching structure deployed in the subject invention for the transfer handling of data related to individual workout records insures, (via database software and the tool set that the gym members records are made available to fitness professionals at the gym and that via tool set/fitness professional combination the member receives stat of the art counseling services. Beyond counseling applications the subject inventions network structure, user authentication functions and records capability will allow individual fitness records to be made available to authorized and interested third parties. In addition the cumulative data base of member user activity and preferences developed for via the system can be "mined" as a data resource for both public and private sector interests.

Lastly, and a the core of the subject invention is a simple easy to use, installable system which provides the means to break the requirement for gym based fitness professional to participate in every member workout in order to effectively counsel that member.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting

DESCRIPTION OF THE DRAWINGS

FIG. 6 is an illustration of an exercise data page shown on the display monitor.

FIG. 7 is an illustration of various exercise equipment showing different sub-routines executed to display different exercise data pages to the member.

DESCRIPTION OF THE PREFERRED EMBODIMENT (S)

Figure 1:
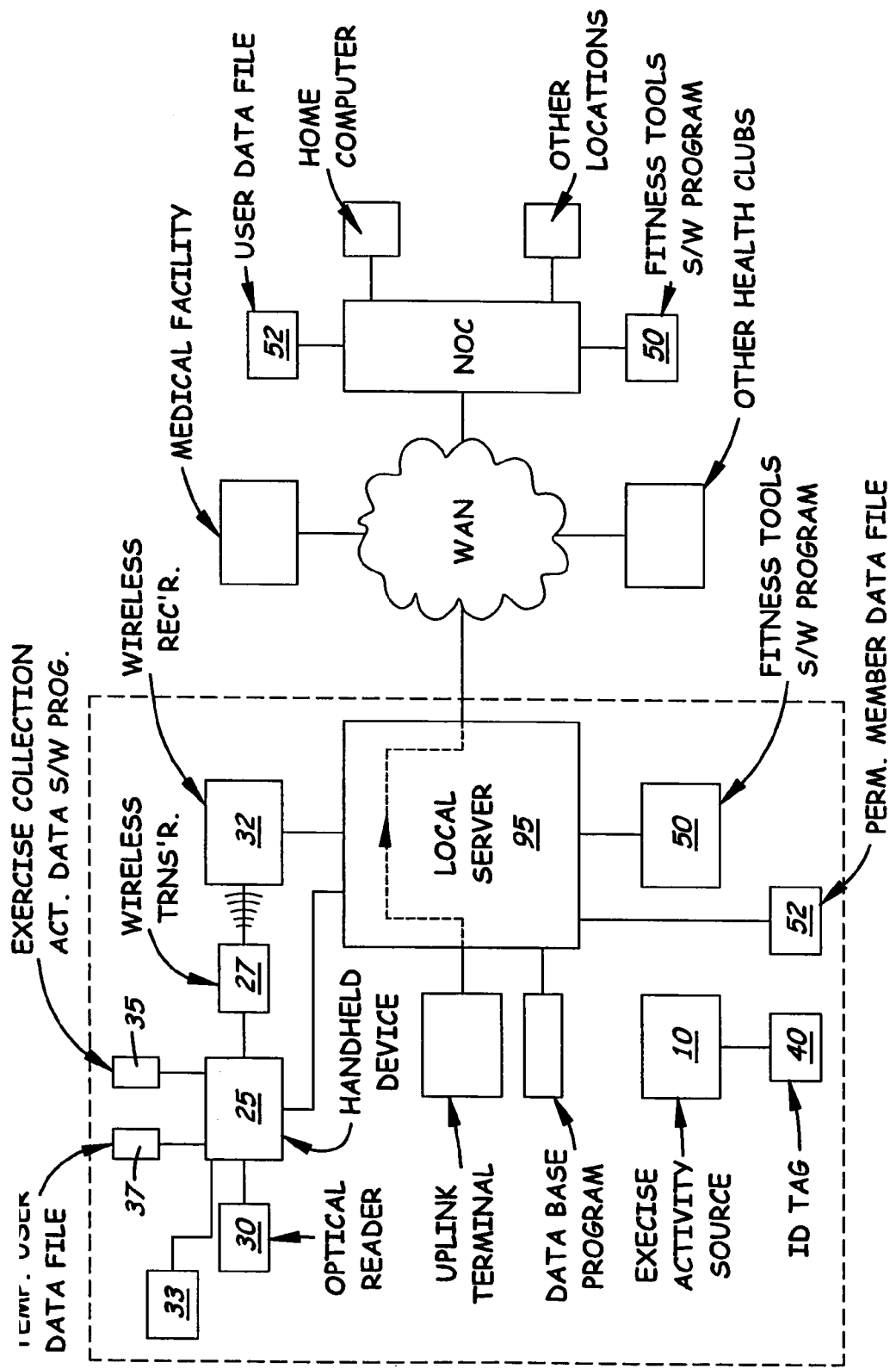
FIG. 1 is an illustration of the health club exercise recording system.
Figure 2:
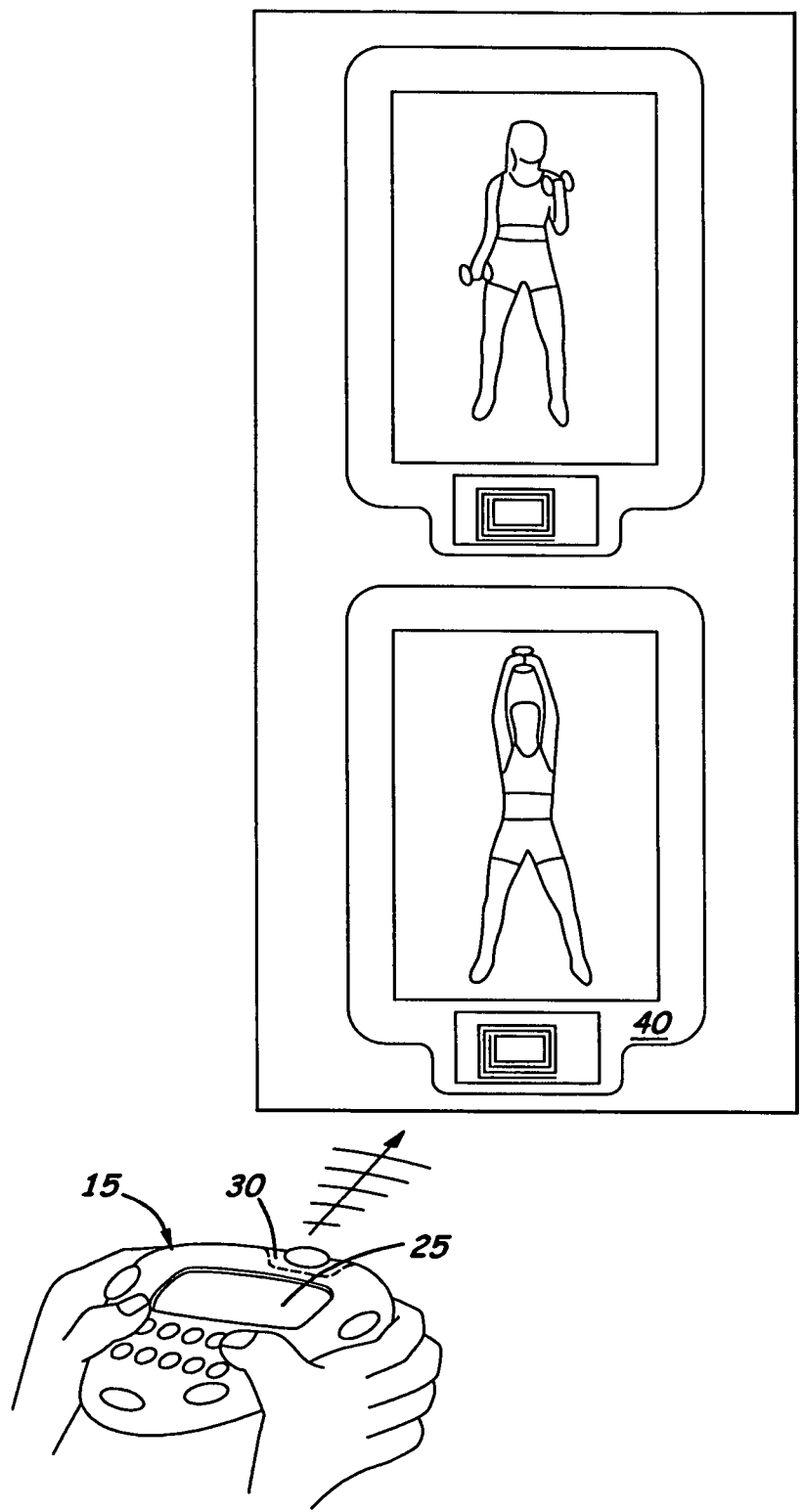
FIG. 2 is a perspective view of the handheld device being used to interrogate an EIDM.

Referring to the accompanying FIGS. 1-8, there is shown a system 10 for easily recording the exercise activities performed with or without exercise equipment that does not require the direct participation of a trainer. The system includes a portable handheld device 15 used to input exercise information that is uploaded to a local server 95. A fitness tools software program 50 loaded into the working memory of the local server 95 is used to collect the uploaded records from the handheld device 15 and store them in a permanent member data file 52. The member or authorized individuals can then use the fitness tools software program 50 to review the member data files to determine the member's fitness or training levels.

The handheld device 15 is lightweight, portable, and ruggedized to make it shock, heat, and moisture tolerant. Loaded into the memory of the handheld device 15 is an exercise data collection software program 35 that activates a built-in exercise identification module interrogation means, referred to as an EIDM interrogation means used to detect a unique EIDM attached to or located in the vicinity of the exercise activity data source. When the EIDM is interrogated, the exercise data collection software program 35 automatically executes a sub-routine 80-85 designed for the specific exercise activity data source 10 which sub-routine includes a date/clock function that automatically records start and stop times and the elapsed time for the exercise, as well as rest intervals between exercises. The sub-routine 80-85 presents one or more data entry pages 60A-60F with a plurality of prompts 61 displayed thereon each designed to sequentially elicit information manually inputted by the member into the handheld device 15. The exercise information is then stored in a temporary member data file 37 on the handheld device 15 that later is uploaded to a local server 95 via an uplink terminal, a wireless communication link or a hardwire connection. Each time the member moves to a new exercise activity data source 10, the EIDM interrogation means and EIDM are used to quickly identify the exercise activity data source 10 and present the proper exercise data entry page 60 and prompts 61 associated therewith.

The exercise data collection software program 37 automatically executes the specific sub-routine 80-85 associated with an identified exercise activity data source 10A-10E (see FIG. 7). The exercise activity data source 10 may include a treadmill 10A, a stair machine 10B, an elliptical machine 10C, free weights 10D, or a weight machine 10E with a single or a plurality of weight stations as shown in FIG. 7. The exercise activity data source 10 may also be a weight lifting station, a basketball court, an aerobic exercise room, a stretching mat or room, a jump rope, a heart rate monitor, a blood pressure monitor, etc. (not shown). When the exercise activity data source 10 is recognized, the exercise data collection software program 35 automatically presents the exercise data page 60 that presents a plurality of prompts 61 suitable for the exercise activity data source 10.

The EIDM interrogation means and EIDM provide a communication link between the handheld device and the exercise equipment. In the preferred embodiment, the EIDM interrogation utilizes an EIDM comprised of a computer chip, a chip housing ("can"), a pictorial representation of the exercise or activity which the subject EIDM is associated with and a "reader/receiver" incorporated within the handheld capable of powering and communicating with the EIDM via a physical contact "1-wire protocol" data exchange link. The EIDM is a compatible ID tag 40, such as a printed identification label/hieroglyph, a radio transducer, or barcodes capable of being detected or interrogated by the EIDM interrogation means.

The local server 95 is designed to receive uploaded temporary member data files 37 from the handheld device 15, use the fitness tools software program 50 to collect and store the member files in permanent member data file 52, and then use the fitness tools software program 50 to evaluate and present the information in the permanent member data file 52 to the member or authorized individuals. In a second embodiment of the system, shown in FIG. 2, the local server 95 is replaced by an uplink terminal that connects to a remote server located in or connected to a network operations center, NOC.

Figure 3:
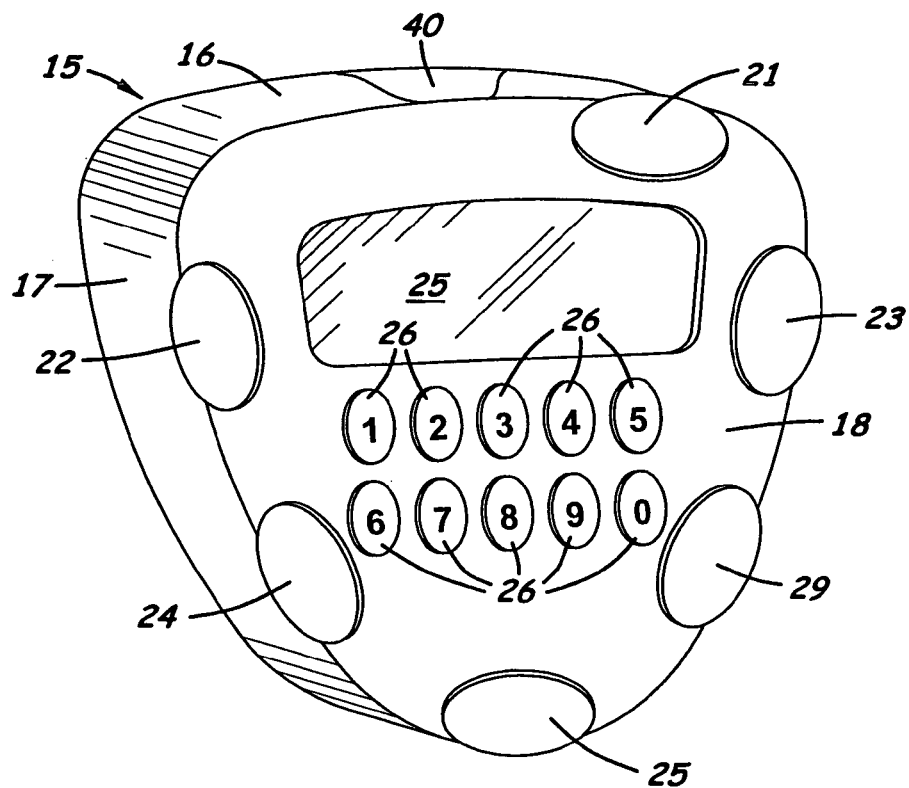
FIG. 3 is a front plan view of the handheld device.
Figure 4:
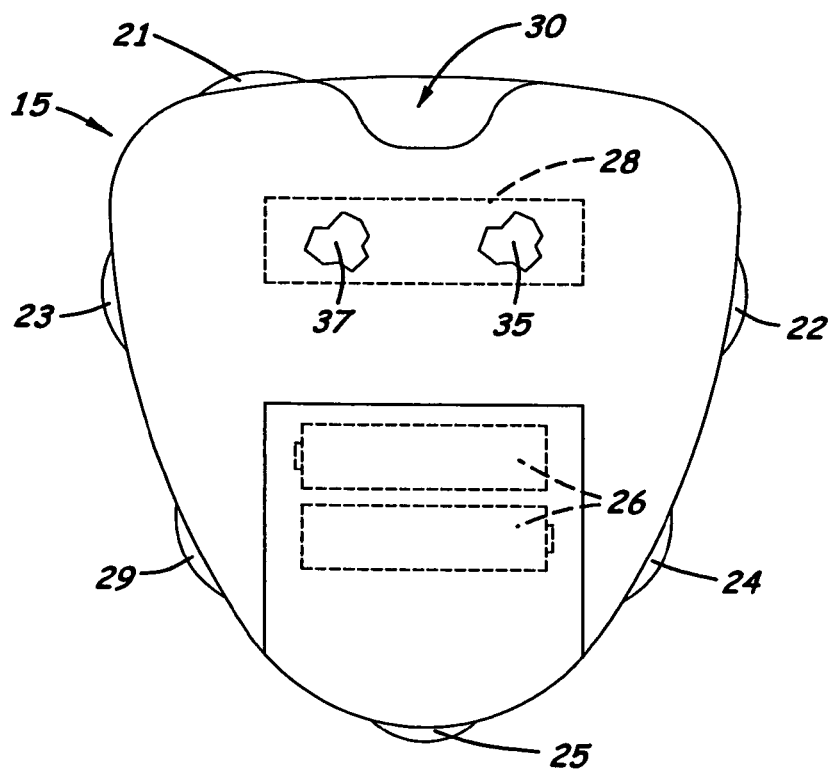
FIG. 4 is a rear plan view of the handheld device.
Figure 5:
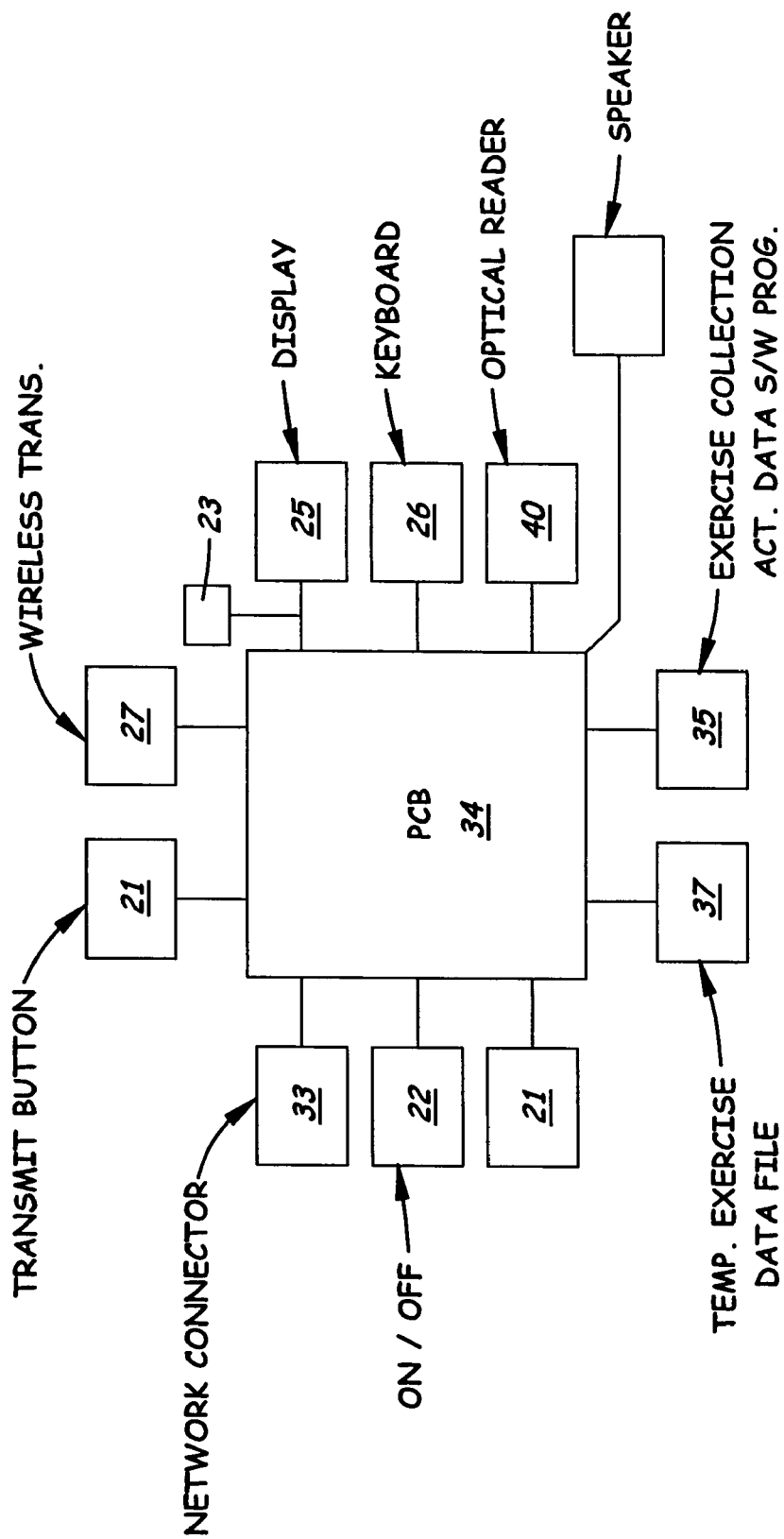
FIG. 5 is a block diagram of the handheld device.

The Network Operations Center (NOC) provides a central repository for the system's data base. In addition, the NOC provides a WAN presence to provide records access for club based fitness professionals working with the system's users. The NOC also provides the WAN presence by which User records input can be made from sources outside of the gym (from home or "on the road"). The NOC also provides system updates, billing as well as network security and document security functions these functions enable delivery of individual exercise records or WAN records access to authorized third parties with and interest in individual or group exercise records, including but not limited to: treating physicians, rehabilitation, therapy professionals, NCAA and other athletic interests, Dept of Defense (e.g. national guard force readiness, corporate wellness incentive programs As shown in FIG. 3, the handheld device 15 includes a display monitor 25 and an input means. In the preferred embodiment, the input means is a set of ten numerical keys 26 located on the front surface 16 of the device 15. In other embodiments, the input means could be a combination monitor and "touch screen" functionality (not shown) with the ten numerical keys displayed thereon. Mounted inside the device 15 are batteries 28 (AA, AAA or 9 Volt) designed to supply a DC electric current. Mounted on the front surface 16 of the device is an "Identification" button 21. Mounted on the side surfaces 17 of the device 15 are a power switch 22 and an optional display monitor brightness switch 23. Mounted on the front surface 16 is a function key 24 and an optical reader activation button 21. Also, mounted on a side 17 or front surface 16 is a small speaker (not shown) to provide audible cues to a member, such as a cadence tone during certain exercises. Mounted on the rear surface 19 is an optional belt clip or hook and loop connector pads (not shown). In other embodiments, a biometric security means, such as a fingerprint reader 25, may be included to prohibit inadvertent use of the handheld device by another member during the course of the exercise session. Also, mounted inside the device 15 is an optional wireless transmitter 27 enabling the device 15 to communicate with a wireless receiver 32 connected to the local server 95. The handheld device 15 may also include an optional network connection port 33 enabling the device 15 to communicate directly with the local server 95 or to the uplink terminal.

During use, the member activates the handheld device 15 and holds the optical reader 30 to read the ID tag 40 to interrogate and identify the fitness exercise activity data source 10. Once the fitness exercise activity data source 10 is identified, the exercise activity collection data software program 35, loaded into the handheld device's working memory, automatically auto-configures the device 15 and presents the proper exercise data page 60 for the fitness exercise activity data source 10. A representative exercise data sheet, shown in FIG. 6, is then presented on the display monitor 25.

On the exercise data page 60 is shown a plurality of prompts 61 that the member responds to after completion of the exercise activity. When the exercise activity is completed, the member manually inputs the data using the keys 26. The inputted exercise activity information is then stored in the temporary member file 37 for later uploading to the central server 95.

As more clearly shown in FIG. 7, each exercise activity data source (10A-10E shown) is assigned a sub-routine 80-84 that presents a specific exercise data page 60 A-E to the display monitor 25. The nature of the prompts 61 may be the same or different. With some exercise equipment or activity, a second sub-routine 85 and a second specific exercise data sheet 60F are presented.

The permanent member data file 55 provides a comprehensive record of his or her cumulative exercise activity and achieved fitness level. This file 55 can then be evaluated and reviewed by club-based fitness professionals to provide a broad range of counseling services to members, and the record can be provided to medical professionals or other third parties away from the fitness center who may have legitimate interests in the fitness level of any particular member.

Figure 8:
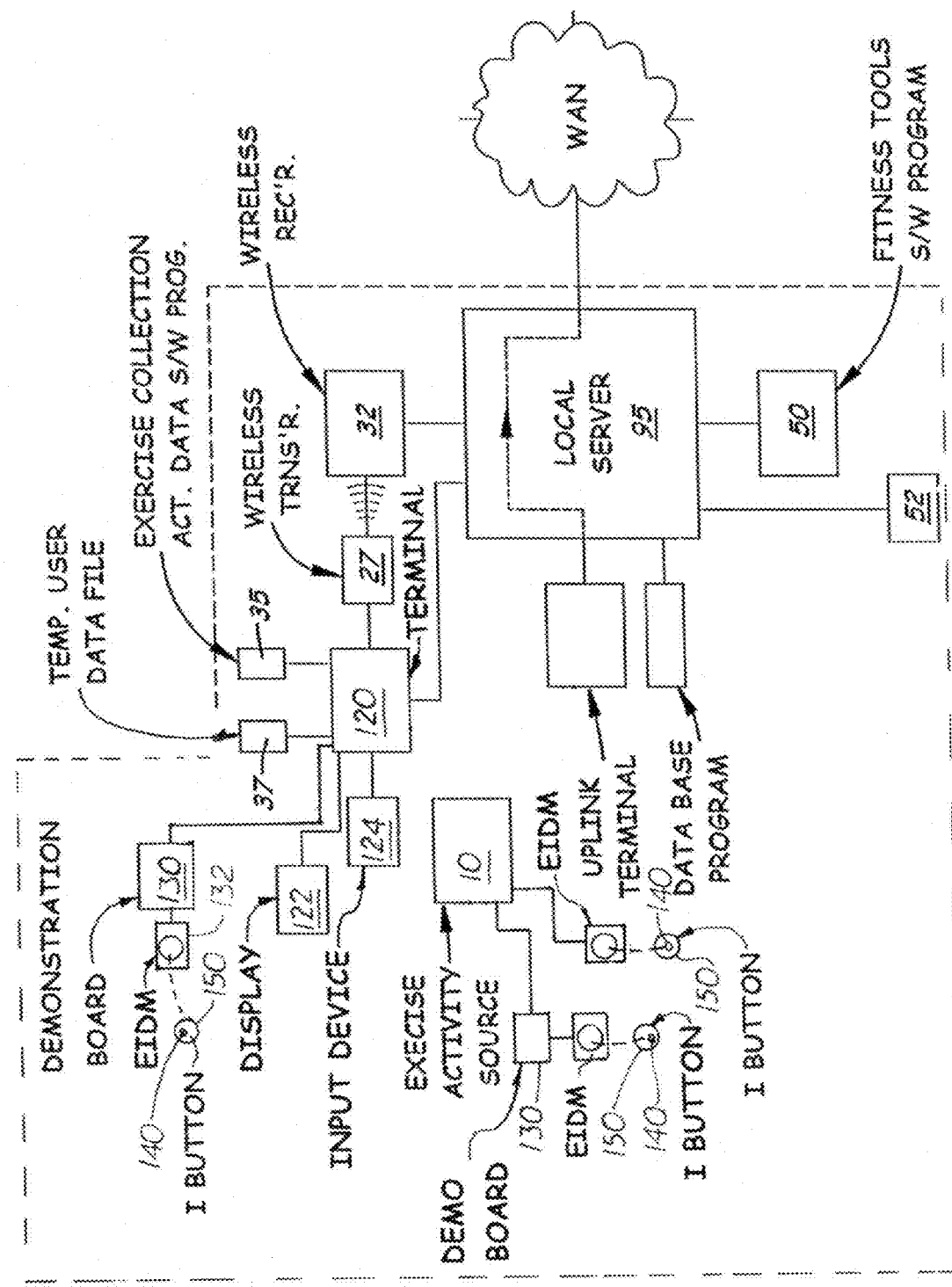
FIG. 8 is an illustration of the second embodiment of the exercise activity recording system.

In another embodiment of the invention, shown in FIG. 8, each piece of equipment, exercise movement area, fitness activity or biometric equipment (called exercise activity source 10) in a facility where exercises are preformed is assigned to an EIDM. Each EIDM is linked or coupled to a stationary terminal 120 connected to or located near the exercise activity source 10. The terminal 120 is coupled to a display 122 and a manual input device 124. Terminal 120 may be used exclusively with one piece of exercise activity source 10 or with a plurality of exercise activity sources. The EIDM associated with each exercise activity source 10 may be located at or near the exercise activity source 10 or it may be mounted on the terminal's front panel or on a single or multiple exercise activity demonstration board 130. Loaded into the memory of the terminal 120 is an exercise data collection software program 35 and a temporary data user file 37.

Each user is assigned a personal identification code 140 which must be manually inputted into the terminal 120 or assigned a portable user identification device 150 that interfaces either directly with the EIDM coupled to the exercise activity source or to the terminal 120, or with an input device 124 attached to linked to the terminal 120.

The user identification device 150 contains the user's personal identification code 140 that must be transmitted to the terminal 120. The terminal 120 then uses the user's personal identification code 140 to determine the user file in which to temporarily store the exercise data. The user's personal identification code 140 may be inputted or transmitted to the terminal 120 before or after the exercise activity source is used.

An example of a portable user identification device 150 assigned to a user is an I-button 150 designed to communicate with a terminal linked I-button 132. During use, the user's I-button 150 is pressed against the terminal linked I-button 132 and automatically transmits the user's personal identification code 140 into the terminal 120. In the preferred embodiment, the terminal I-button 132 is also linked to a specific exercise activity source so that it also acts as an EIDM, which, when activated by the user's I-button 150, simultaneously informs the terminal 120 which exercise activity source is selected and identifies the user to the terminal 120.

In the terminal based embodiment, when the EIDM is activated, a sub-routine and one or more prompts relating to the exercise activity source are then presented on the terminal's display 122. The user then manually inputs the exercise performance information into a manual input device 124 coupled to the terminal 120 in response to the prompts.

In this embodiment, the mobile and fixed components of the system are reversed with respect to the first embodiment described above. When the user activates the EIDM, a data exchange sequence is initiated in the terminal which initiates a user input identification exchange and a sub-routine specific to the exercise activity source. The identification sequence is directed towards identifying the system user to the terminal and to the specific exercise selected by the system user. The EIDM is now in a fixed location as are the terminal 120 with the exercise data program, the exercise specific sub-routines and the processor. The only mobile component is the user's electronic identification device. Also, inputted information may be stored in the terminal 120 or immediately transmitted to a permanent member data file on a local or remote server.

In both embodiments, the complete member records generated by system in combination with a centralized database for the system's records storage and records access support the development and application of a set of software tools which will be regularly update with the most current fitness information. The tool set is directed toward providing the fitness professional working with a user with the following information with which to counsel that user toward the safes most effective, most fun usage of his/her time in the gym.

- Allocation of time in the gym (strength vs. cardio) (legs vs. arms) (back vs. stomach) etc;
- Strength and muscle balance between various muscle groups
- Joint usage during work outs;
- Increases or decreases in muscle strength, flexibility or endurance
- Allocation of repetitions between muscle groups;
- Changes in time of day for workout, work out duration, rest time between individual exercises; and,
- Changes is any of the forgoing as they relate to modifications in work out activity as a result of an event recorded by the User into the system or as the result of a fitness professional's input to the User by way of preferred changes to the Users work out regime.

The system Tool will review User health and fitness activity and performance against "norms" for his/her age sex, time in the gym, Etc. Tools will high light "trouble areas" identified by this analysis and offer the fitness counselor input as to possible changes to the Users exercise activity.

The system tool will review User health and fitness activity and performance against inputs to the Users personal exercise record by health healthcare professionals, therapists etc. and display areas of concern or interest unique to that specific user.

SYSTEM OPERATION

The following operating scenario describes the system using the first embodiment of the system that uses an exercise identification module interrogation means and the EIDM as an optical reader 30 and ID tag 40, respectively. It should be understood, however, that the optical reader 30 and ID tag 40 could be replaced with a radio frequency or infrared transmitter and receiver or other wireless or physical contact/hardwire transmitting and receiving devices medium for wireless communication between the handheld device and the exercise activity data source's EIDM.

Prior to commencing the exercise activity, the member activates the EIDM component on the handheld. When the exercise activity data source 60 is identified, the sub-routine associated 80-84 with the exercise activity data source 10 is automatically executed. The exercise data page prompts 61 are then sequentially presented on the display monitor 25. The member enters data in response to prompts 61 displayed on the handheld device 15 for temporary storage in the handheld device 15 relative to the specific exercise. The member repeats this recording process for each exercise performed throughout the course of the exercise sessions. Upon completion of the exercise session, the temporary data files are uploaded into the member's permanent exercise activity file on the local central server 95. Alternatively, the handheld device is placed in the uplink terminal which automatically uploads the temporary data files to the member permanent files on a central server on the NOC. The fitness tools program is then used to review the permanent files and issue comments and recommendations to the member.

With the second embodiment of the system that uses a terminal 120, the user first selects and exercise using the EIDM on located on or near the exercise activity source, on the terminal, or a demonstration board setup near the terminal 120. The user then exercises on or with the exercise activity source. When the exercise is completed, the user manual inputs his or her identification code into the input means connected to the terminal 120. If the user uses a user and terminal I-buttons, the steps of selecting an EIDM associated with the desired exercise activity source and the user's identification information are combined. After the EIDM is selected, one or more the user then inputs exercise specific data in response to the prompts. The user repeats this recording process for each exercise performed throughout the course of the exercise sessions. Upon completion of the exercise session, the temporary data files are uploaded into the member's permanent exercise activity file on the local central server 95.

In summary, the method of collecting, transmitting, and recording an exercise routine comprising the following steps: (1) selecting an exercise activity data source each assigned a unique EIDM; (2) selecting a handheld device 15 or a terminal 120 with user identification input means, said handheld device or terminal including an exercise activity data collection software program 35 and an exercise identification module interrogation means, said exercise activity data collection software program 35 used to automatically execute a plurality of prompts 61 that request activity information for each unique EIDM and store the exercise activity information in a temporary member file 37; (3) connecting the handheld device or terminal to a server 95 and uploading the data in the temporary member file to a permanent member file; (4) loading a fitness tools software program 50 into said server 95, said fitness tools program 50 used to evaluate and review the data in the permanent member file 37 to determine the fitness level of a member and recommend future exercises.

While a preferred embodiment of the exercise recording system has been described in detail, it should be apparent that modifications and variations thereto are possible, all of which fall within the true spirit and scope of the invention. With respect to the above description then, it is to be realized that the optimum dimensional relationships for the components of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, the term "exercise activity data source" is used to encompass every exercise equipment activity or non-equipment activity. The term "wireless communication link and EIDM" are meant to encompass all means of wireless communication in which an exercise activity is recognized by the handheld device or terminal. Therefore, the foregoing is considered as illustrative only of the principles of the invention.

We claim:

1. A physical exercise records system, comprising:
   a. a plurality of exercises activity data sources;
   b. a unique identifying EIDM associated with each said exercise activity data source;
   c. a terminal linked or coupled to each said EIDM used with said exercise data sources, said terminal including a display, means for inputting data into said terminal, means for identifying an means for identifying a user, and working memory; and,
   d. an exercise software program loaded into said working memory of said terminal, said exercise software program runs a plurality of sub-routines each associated with one said EIDM, said sub-routines presents on said display at least one exercise data entry page after said EIDM is identified and interrogated that queries a user to input exercise activity data relevant to the exercise activity data source.

2. The physical exercise records system, as recited in claim 1, wherein said unique identifying EIDM associated with each said exercise activity data source is an identification contact button.

3. The physical exercise records system, as recited in claim 2, wherein said identification contact button is attached to said exercise activity data source.

4. The physical exercise records system, as recited in claim 2, wherein said means for identifying a user is a contact button manually pressed against said contact button attached to said exercise activity data source.

5. The physical exercise records system, as recited in claim 3, wherein said means for identifying a user is an identification contact button assigned to a specific user that is selectively pressed against said contact button attached to said exercise activity data source.

6. The physical exercise records system, as recited in claim 2, wherein said identification contact button is attached to said terminal.

7. The physical exercise records system, as recited in claim 2, wherein said means for identifying a user is a contact button manually pressed against said contact button attached to said exercise activity data source.

8. The physical exercise records system, as recited in claim 7, wherein said means for identifying a user is an identification contact button assigned to a specific user that is selectively pressed against said contact button attached to said exercise activity data source EIDM interrogation means and said EIDM is an optical reader and a compatible tag element capable of being interrogated by said optical reader.

9. The physical exercise records system, as recited in claim 1, wherein said EIDM interrogation means and said EIDM is a RFID reader and compatible tag element.

10. The physical exercise records system, as recited in claim 1, further including a server capable of receiving the input records from said terminal.

11. The physical exercise records system, as recited in claim 10, further including a wireless communication link between terminal and said server.

12. A physical exercise records system, comprising:
    a. an exercises activity data source;
    b. an exercise coupled electronic contact identification button coupled to said exercise activity data source:
    c. a terminal linked or coupled to said exercise coupled electronic contact identification button couple to said exercise activity data source, said terminal including a display, means for inputting data into said terminal, means for identifying an means for identifying a user, and working memory; and,
    d. an exercise software program loaded into said working memory of said terminal, said exercise software program runs a plurality of sub-routines each associated with one said EIDM, said sub-routines presents on said display at least one exercise data entry page after said EIDM is identified and interrogated that queries a user to input exercise activity data relevant to the exercise activity data source.

13. A method for recording and monitoring exercise activities by members of a exercise facility that contains a plurality of exercise activity data sources each associated with an identifiable EIDM, said exercise facility includes at least one terminal coupled to said EIDM's used with a plurality of terminals, said terminal includes a display, a data input means, and a software program that executes a EIDM specific sub-routine that requests specific exercise performed at exercise activity data source to be manually inputted into said terminal, said method comprising:
    a. selecting an exercise activity data source coupled or linked to an EIDM and to said terminal;
    b. performing an exercise with said exercise activity data source;
    c. identifying the user on said terminal; and,
    d. inputting data into said display on said terminal in response to said sub-routine page that pertains to the exercise performed with said exercise activity data source.

* * * * *